US008721724B2

(12) United States Patent
Lechmann et al.

(10) Patent No.: US 8,721,724 B2
(45) Date of Patent: May 13, 2014

(54) MODULAR INTERVERTEBRAL IMPLANT

(75) Inventors: Beat Lechmann, Grenchen (CH); Robert Frigg, Bettlach (CH)

(73) Assignee: DePuy Synthes Products, LLC, Raynham, MA (US)

( * ) Notice: Subject to any disclaimer, the term of this patent is extended or adjusted under 35 U.S.C. 154(b) by 1801 days.

(21) Appl. No.: 11/769,273

(22) Filed: Jun. 27, 2007

(65) Prior Publication Data

US 2007/0250168 A1 Oct. 25, 2007

Related U.S. Application Data

(63) Continuation of application No. PCT/CH2005/000775, filed on Dec. 27, 2005.

(30) Foreign Application Priority Data

Dec. 28, 2004 (CH) .......................................... 2161/04

(51) Int. Cl.
*A61F 2/44* (2006.01)

(52) U.S. Cl.
USPC .......................................................... 623/17.16

(58) Field of Classification Search
USPC .............................................. 623/17.11–17.16
See application file for complete search history.

(56) References Cited

U.S. PATENT DOCUMENTS 5,534,029 A * 7/1996 Shima ........................ 623/17.15
5,676,701 A * 10/1997 Yuan et al. ................. 623/17.15
5,782,832 A * 7/1998 Larsen et al. .............. 623/17.11
5,895,428 A * 4/1999 Berry ......................... 623/17.15
6,368,350 B1 * 4/2002 Erickson et al. ........... 623/17.14
6,447,548 B1 * 9/2002 Ralph et al. ................ 623/17.16
6,517,580 B1 * 2/2003 Ramadan et al. .......... 623/17.15
7,637,955 B2 * 12/2009 Marik et al. ............... 623/17.14
2005/0187633 A1 * 8/2005 Ferree ........................ 623/17.15
2005/0216086 A1 * 9/2005 Marik et al. ............... 623/17.15
2006/0241772 A1 * 10/2006 Buettner-Janz et al. ... 623/17.15
2006/0265068 A1 * 11/2006 Schwab ..................... 623/17.11
2007/0250168 A1 * 10/2007 Lechmann et al. ........ 623/17.11

FOREIGN PATENT DOCUMENTS

FR 2 718 635 A1 10/1995
WO WO 02/11650 A2 2/2002

OTHER PUBLICATIONS

International Search Report, dated Mar. 31, 2006, in International patent appln. No. PCT/CH2005/000775.
International Preliminary Report on Patentability and Written Opinion of the International Searching Authority in appln. No. PCT/CH2005/000775 (Jul. 3, 2007).

* cited by examiner

*Primary Examiner* — Mary Hoffman
(74) *Attorney, Agent, or Firm* — Meunier Carlin & Curfman, LLC

(57) ABSTRACT

A modular intervertebral implant including a first and second component connectable in a ball-joint like manner. The first component having a first surface configured to abut an end plate of a first adjoining vertebral body and a concave spherical articulation surface with a radius R. The second component having a second surface configured to abut an end plate of a second adjoining vertebral body and a convex spherical articulation surface with substantially the same radius R as the concave spherical articulation surface.

15 Claims, 5 Drawing Sheets

MODULAR INTERVERTEBRAL IMPLANT

CROSS REFERENCE TO RELATED APPLICATION

This application is a continuation application of International Application Serial No. PCT/CH2005/000775 filed on Dec. 27, 2005 for "MODULAR INTERVERTEBRAL IMPLANT" which is based upon Swiss Application No. 2161/04 filed on Dec. 28, 2004 each of which is hereby incorporated by reference herein.

FIELD OF INVENTION

The invention relates to an intervertebral implant, particularly an artificial intervertebral disc.

DESCRIPTION OF RELATED ART

Today implants or prostheses are inserted into the intervertebral space of two adjoining vertebral bodies after removal of an affected natural intervertebral disc or an affected nucleus pulposus of an intervertebral disc. It is the object of the implantation of such implants to regain the natural qualities as well as possible, i.e. particularly the original height of the intervertebral disc and consequently the original distance between the two adjoining vertebral bodies. Furthermore, motions of the adjoining vertebral bodies relative to each other shall be permitted in their natural quality without being impeded. For this reason a conservation of the possibility of motion in case of forward/backward bending, i.e. flexion and extension of the vertebral bodies as well as in case of a lateral bending of the vertebral bodies within the natural limits is essential. Furthermore, the natural ligaments and muscles along the vertebra essentially remain intact, so that they further stabilize the motions of a mechanical substitute of the intervertebral disc.

Such an intervertebral implant is known from U.S. Pat. No. 5,314,477 MARNAY. This known implant comprises two plates being connected by means of a ball-joint. Since only one size of the implant as well as only one value for the radius of the articulation surfaces is provided the centre of rotation of the implant as well as its kinematics are predefined so that the surgeon may not individually adapt these qualities to the needs, respectively the anatomy of the patient. Furthermore, these implants are not configured to adapt the centre of rotation of the spherical cap to the individual anatomical requirements.

SUMMARY OF THE INVENTION

Accordingly, it is the principal object of the present invention to provide an intervertebral implant permitting an optimal movability of the adjacent vertebral bodies as well as to take into consideration the individual physiology of the patient to be treated.

To achieve the above object the present invention relates to a modular intervertebral implant and more particularly to an artificial intervertebral disk comprising two components being mutually connectable in a ball-joint like manner. The first and second components are provided with an apposition area each, said apposition area being apt for abutment to the end plates of the adjoining vertebral bodies. Furthermore, said first and second components are provided with a concave, respectively a convex spherical articulation surface having the same radius R. The first and second component have a maximum height $H_1$, respectively $H_2$, such that a maximum overall height $H<(H_1+H_2)$ results for the assembled intervertebral implant. Allowing a suitable quality of motion of the adjacent vertebral bodies the intervertebral implant is provided with a centre of rotation RZ which has a shortest distance A to the second apposition area, said shortest distance A being equal to the absolute value of $(H_2-R)$, and said first and second components are selected from a first kit of at least $M\geq 2$ first components having different heights $H_1$, respectively from a second kit of at least $N\geq 2$ second components (4) having different heights $H_2$, such permitting a selection of the distance A of the centre of rotation RZ through a selection of the radius R and the maximum height $H_2$ of the second component.

The intervertebral implant according to the invention offers the following advantages compared to the known devices:

- it permits an individual adaptation of the joint implant for any arbitrary pair of vertebral bodies. By means of this adaptation the individual anatomy of the natural moving element may be taken into account by selecting appropriate first and second components;
- the individual segmental sequences of motion may be preoperatively considered and determined by the surgeon;
- a more convenient surgical procedure is permitted;
- the position of the centre of rotation, the tilting and the translational motion of the intervertebral implant may be arbitrarily selected within a relatively wide range;
- the position of the centre of rotation is adjustable in its distance to the second apposition area, since both components are modularly configurable; and
- the components being used as modules may also vary in their radius of the spherical segment.

The intervertebral implant according to the invention is implantable into the intervertebral space by means of one or two posterior approaches because the implant is configured in two-piece form such that the two components are implantable mutually independently into the intervertebral space through the two separate approaches. The similar implantation procedure is anteriorly applicable, particularly in the higher lumbar as well as in the thoracolumbar section. The anatomical conditions do not allow an insertion from strict anterior, since the aorta and the vena cava impede the approach. In this case the ventral structure of the annulus fibrosus as well as the anterior longitudinal ligament are being kept intact, as well.

In a preferred embodiment the two kits of first and second components of the intervertebral implant are configured such that the overall height H is constant for any combination of a first component with a second component. The advantages of this embodiment are essentially to be seen therein that in case of a predetermined constant overall height the centre of rotation of the intervertebral implant may be dislocated within certain limits thereby allowing different ranges of motion of the involved vertebral bodies.

In a further embodiment all components of the two kits are provided with the same radius R. The advantages of this embodiment are that the coincidence of the radii R of the spherical caps enables the bearing to act as a slideable surface bearing for each arbitrary combination of a first and a second component, causing less abrasion due to the decreased surface pressure compared to a line contact bearing as in case of different radii R.

In a further embodiment the first components of the first kit are provided with radii R of the same length. The advantages of this embodiment are that the position of the centre of rotation on the central axis is adjustable solely through the height of the two components.

In a further embodiment the first components of the first kit are provided with radii R of different length. The advantages of this embodiment are that the position of the centre of rotation on the central axis is adjustable solely through a variation of the radius R independently of the height of the two components.

In a further embodiment the distance A of the centre of rotation to the second apposition area is about 30% of the maximum overall height. The advantages of this embodiment are essentially to be seen therein that the translational part of motion, respectively the relative motion between the two components transversely to the central axis in case of an excursion are small—with regard to the physiology being specific for a patient. In this particular case the facet joints are arranged relatively steeply with respect to the spinal cord.

In a further embodiment the distance A of the centre of rotation RZ to the second apposition area is about 600% of the maximum overall height H. The advantages of this embodiment are essentially to be seen in the fact that in case of radii of the spherical cap having such high dimensions the excursion of the first and second member relative to each other is a limiting type to a pure translation. Regarding the patient specific physiology the translational part of motion between the two components, respectively the relative motion transverse to the central axis is high in case of an excursion. In such cases the facet joints are disposed with a relatively low gradient with respect to the spinal cord.

In yet another embodiment the centre of rotation RZ is located inside the second component and the difference ($H_2$−R) has a positive value. The advantages of this embodiment are essentially to be seen in the fact that such a configuration results in a small radius of the spherical cap, consequently resulting in a relatively small translational part of motion between the two components, i.e. a small mutual displacement transverse to the central axis in case of a mutual rotation of the two components about the centre of rotation RZ. In case of facet joints having a high gradient (in case of an upright patient) the articulation surfaces are taken care of since no compression arises during flexion- or extension motions. Preferably, the distance A inside the second component is a minimum of 0.5 mm, respectively to a maximum of 5 mm.

In still another embodiment the centre of rotation RZ is located outside of the second component and the difference ($H_2$−R) has a negative value. The advantages of this embodiment essentially are the resulting relatively large radii of the spherical cap consequently resulting in a relatively high translational part of motion between the two components, i.e. a high relative displacement transverse to the central axis. In case of facet joints having a low gradient (in case of an upright patient) the articulation surfaces are taken care of since no compression arises during flexion- or extension motions. Preferably, the distance A outside of the second component is a minimum of 1 mm, respectively to a maximum of 95 mm.

In yet another embodiment the first component is configured as a plate like base body with a recessed concave spherical articulation surface and the second component is configured as a plate like base body with a protruding spherical segment.

In a further embodiment the radius of the spherical segment of the second component is between 3 mm and 100 mm, preferably between 4 mm and 20 mm.

In still a further embodiment the second component consists of a metal—plastic material combination.

In another embodiment the convex spherical articulation surface is coated with titanium carbide or amorphous carbon (ADLC).

In yet another embodiment the apposition areas are coated with titanium.

In a further embodiment the apposition areas are convexly shaped.

In still a further embodiment the apposition areas are provided with projections, which comprise at least one wedge like rip being symmetrical to the center plane of the implant and which is standing on the respective apposition area parallel to a straight line in the center plane. The projections may comprise saw-tooth like indentations, which are arranged symmetrically to the center plane. The volume of one projection may be between 0.12 $mm^3$ and 1.4 $mm^3$.

Furthermore, the projections may be at least partially coated with hydroxyl apatite or with a bi-phase hydroxyl apatite—calcium phosphate mixture.

In another embodiment the two components have a mutually facing intermediate surface each whereby these intermediate surfaces are tiltable relative to each other within a range of 0° to 12°.

In yet another embodiment the two components have a centre of gravity each, and wherein upon rotation of the two components relative to each other said centres of gravity perform a translation T relative to each other measured perpendicularly to the central axis and being dependent on the radius R, whereby the translation T is in the range of 0.5 mm to 12.0 mm.

Further objects and advantages of the invention will become apparent from the following description when read with reference to the accompanying drawings which illustrate several embodiments of the invention. In the drawings.

Figure 1:
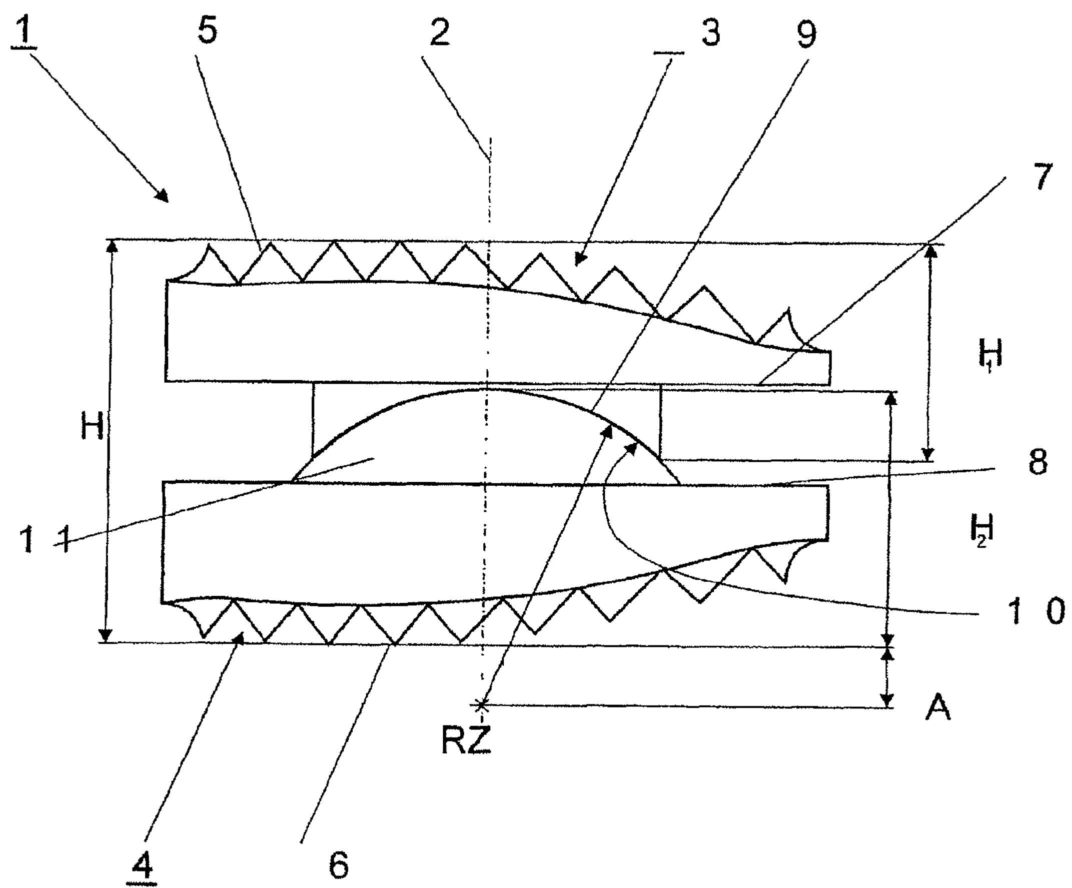
FIG. 1 is a sectional view of an embodiment of the intervertebral implant according to the present invention.

The embodiment shown in FIG. 1 essentially comprises an intervertebral implant 1 with a central axis 2, said intervertebral implant 1 having two components 3;4, whereby the first component 3 consists of a one-piece plate comprising a first apposition area 5 and oppositely arranged an intermediate surface 7 with a concave spherical articulation surface 9. The second component 4 essentially consists of a plate, comprising a second apposition area 6 and oppositely arranged an intermediate surface 8, said second component 4 further comprising a spherical segment 11 being placed upon its intermediate surface 8. The spherical segment 11 is provided with a convex spherical articulation surface 10 apt as a bearing surface permitting slideable motion relative to the concave spherical articulation surface 10.

The mutual tilting of the two components 3;4 around the centre of rotation RZ which is situated on the central axis 2 is limited by the fact that the mutually facing intermediate surfaces 7;8 come at rest at each other if the maximum angle of tilting is achieved. The two apposition areas 5;6 are convexly curved in a manner that an optimal fit to the end plates of the adjoining intervertebral bodies is achieved. Apart from the mutual tilting movement the joint connection between the two components 3;4 further permits a free mutual rotation of the two components 3;4 about the central axis 2.

The spherical segment 11 located between the two components 3;4 together with the concave spherical articulation surface 9 form an articulating connection, whereby the radii R of curvature of the concave spherical articulation surface 9 and the convex spherical articulation surface 10 are equal to each other.

The intervertebral implant has a maximum overall height H, whereby the first component 3 has a maximum height $H_1$ measured parallel to the central axis 2 and the second component 4 has a maximum height $H_2$ measured parallel to the central axis 2 as well. The shortest distance A extends coaxially to the central axis 2 and extends between the centre of rotation RZ located on the central axis 2 and the second apposition area 6.

Figure 2:
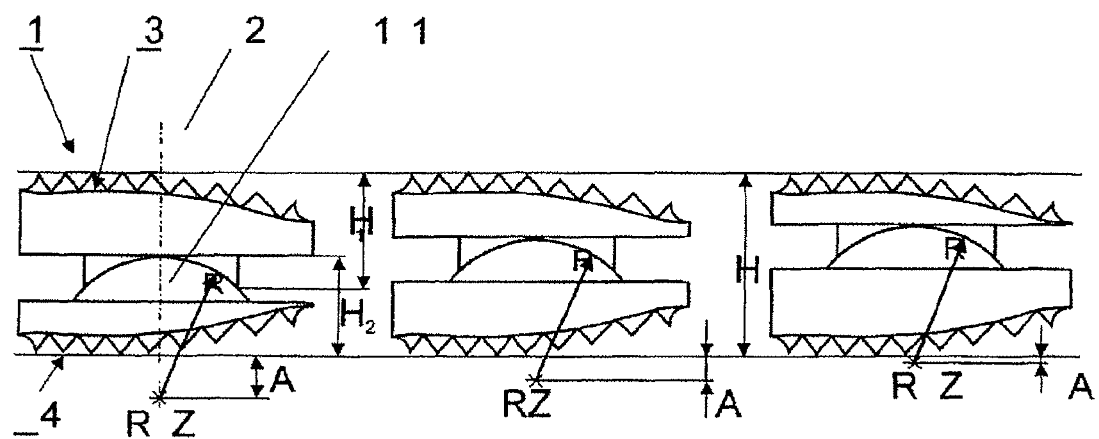
FIG. 2 shows three cross-sections through a series of embodiments of intervertebral implants according to FIG. 1, said intervertebral implants having spherical segments with equal radii, equal overall heights H but different maximum heights $H_1$ and $H_2$ of the components.

A series of three cross-sections of the intervertebral implant 1 illustrated in FIG. 2 shows three different combinations of first and second components 3;4 having different maximum heights $H_1$ and $H_2$ each, whereby the length of the radius R of the spherical segments 11 remains unchanged. The shortest distance A measured coaxially to the central axis 2 between the centre of rotation RZ and the second apposition area 6 varies for the different maximum heights $H_1$ and $H_2$ of the two components 3;4, whereby the maximum overall height H remains constant. The maximum height $H_1$ of the first component 3 increases from left to right in the series shown here, while the maximum height $H_2$ of the second component 4 simultaneously decreases correspondingly so that the overall height H remains constant.

Figure 3:
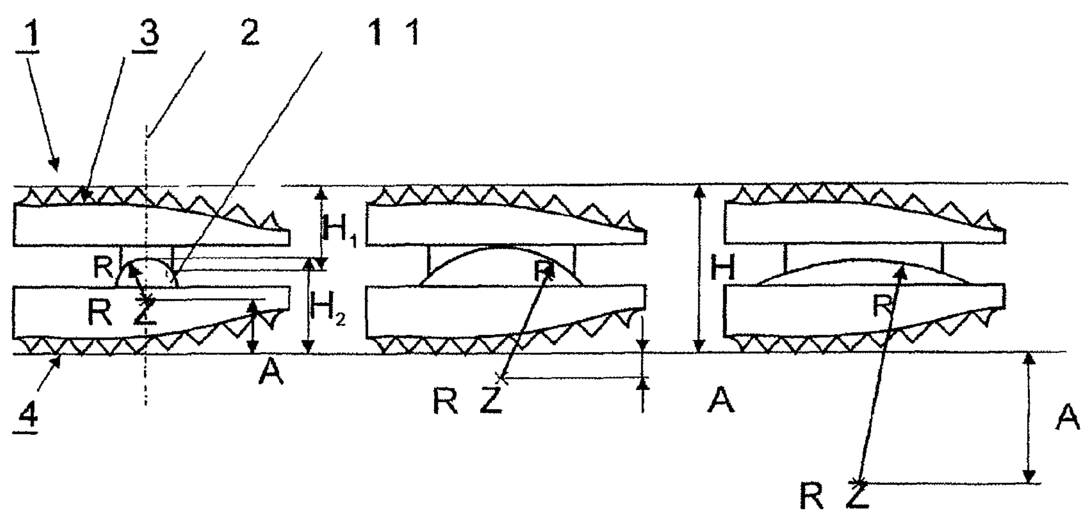
FIG. 3 shows three cross-sections through a series of embodiments of intervertebral implants according to FIG. 1, said intervertebral implants having an equal overall height but each pair of articulation surfaces has a different radius.

The series of three cross-sections of the intervertebral implant 1 illustrated in FIG. 3 shows three different combinations of first and second components 3;4 having different lengths of the radius R and of the shortest distances A. The maximum height $H_2$ of the second component 4 decreases from left to right, whereby the length of the radius R increases and whereby the centre of rotation RZ simultaneously moves along the central axis 2 in such manner that the distance A increases. Through the increasing distance A, respectively the dislocation of the centre of rotation RZ the sliding motion of the concave spherical articulation surface 9 on the convex spherical articulation surface 10 and hence, the motion of the two adjacent vertebral bodies, is being influenced.

Figure 4:
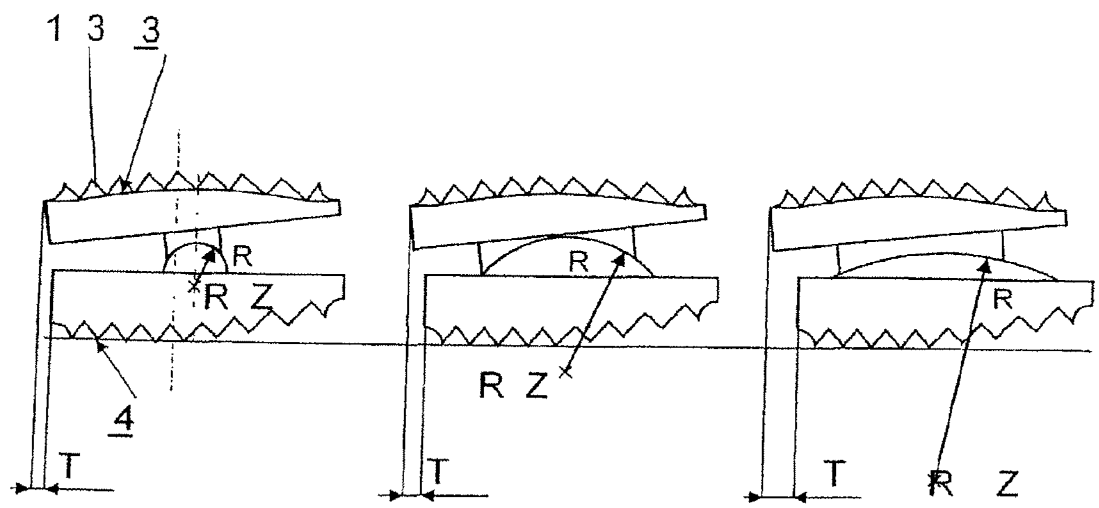
FIG. 4 shows three cross-sections through a series of embodiments of intervertebral implants according to FIG. 1, said intervertebral implants having an equal overall height but each pair of articulation surfaces has a different radius therewith permitting a translation between the two components.

The series of three cross-sections of the intervertebral implant 1 illustrated in FIG. 4 shows three different combinations of first and second components 3;4 having different lengths of the radius R and different ranges of the translational motion T, whereby the translational motion T is defined through the displacement of the centres of gravity of the two components 3;4 measured perpendicularly to the central axis 2 due to a mutual rotation of the two components 3;4. The maximum height $H_2$ of the second component 4 decreases from left to right, whereby the length of the radius R increases. Through the increasing radius R, respectively the movement of the centre of rotation RZ the sliding motion of the concave spherical articulation surface 9 on the convex spherical articulation surface 10 is being influenced and the quality of motion of the two adjacent vertebral bodies is altered. In the embodiment described here the apposition areas 5;6 are provided with macroscopic structures, which are configured as protrusions 13, for example as pyramid like protrusions.

Figure 5:
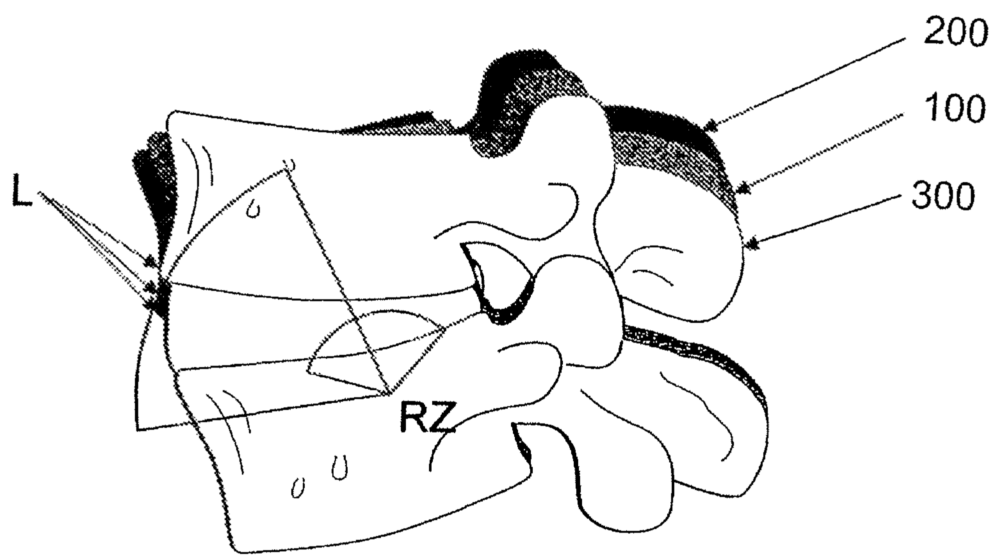
FIG. 5 shows a schematic view of the pre-operative study and analysis of the X-ray images.

FIG. 5 schematically shows the series of X-ray images of the portion of the vertebra to be treated during the preoperative study, whereby the point L indicates an anatomical land mark at the upper vertebral body. The different positions of the anatomical land mark L in case of a neutral position 10, an extension 300 and a flexion 200 of the vertebra define three points, said three points define a circle which is subsequently used in order to determine the centre of rotation RZ and the spherical segment 11.

To select appropriate first and second components for the intervertebral implant to be inserted in the intervertebral space of the patient the following planning and preoperative study is performed. The basis for the determination of the centre of rotation RZ and of the radius R of the spherical segment 11 is the fact that a circle is defined by three points, said circle being defined through the geometrical construction of a circumcircle of a triangle ABC. The circumcentre of the required circle corresponds to the centre of rotation RZ and is defined through the point of intersection of the three perpendicular bisector of the sides AB, BC and AC of the triangle. There is exactly one solution.

The preoperative planning including the above determination of the centre of rotation RZ and of the radius R is then performed as follows:

1. acquisition of three lateral X-ray images of the patient (neutral position 100, flexion 200 and extension 300);
2. definition of an anatomical landmark at the upper vertebral body;
3. registration of the three points defined by the position of the anatomical landmark on the three X-ray images on a neutral image;
4. geometrical construction of the circumcentre of the circumcircle on the neutral image and subsequent determination of the radius R.

In case of insertion of an intervertebral implant 1 between two intervertebral bodies the superior end plate of the lower vertebral body serves as a basis while at the upper vertebral body the anatomical landmarks L are defined in order to reconstruct the motion of the upper vertebral body relative to the lower vertebral body. The motion of the upper vertebral body is defined through three points and as described above the spherical element 11 corresponding to the natural spherical cap of the intervertebral disc may be determined. The centre of rotation RZ of the spherical element 11 of the intervertebral implant coincides with the centre of the natural spherical cap therewith permitting the supporting quality of the intervertebral implant 1. The centre of rotation RZ of the intervertebral implant 1 coincides with the circumcentre defined by means of the study of motion.

What is claimed is:

1. A modular intervertebral implant having a central axis comprising:

a first component selected from a first group of at least two first components with unequal heights wherein the first component has a first height $H_1$, a first surface configured to abut an end plate of a first adjoining vertebral body, and a concave spherical articulation surface with a radius R; and a second component selected from a second group of at least two second components with unequal heights wherein the second component has a second height $H_2$, a second surface configured to abut an end plate of a second adjoining vertebral body, and a convex spherical articulation surface with substantially the same radius R as the concave spherical articulation surface; wherein:

the first component and the second component are connectable in a ball-joint like manner, and wherein the first component and the second component form a center of rotation RZ for said intervertebral implant which center of rotation RZ differs based on the second component selected; and wherein the center of rotation RZ has a shortest distance A to the second surface that is equal to the absolute difference between the height $H_2$ of the second component and the radius R of the second component selected; and wherein a maximum overall H of the intervertebral implant is less than $H_1+H_2$.

2. The intervertebral implant according to claim 1, wherein the combined height ($H_1+H_2$) of the first component selected from the first group and the second component selected from the second group is constant for predetermined combinations of a first component with a second component.

3. The intervertebral implant according to claim 1, wherein all of the components of the first and second groups have the same radius.

4. The intervertebral implant according to claim 1, wherein the concave spherical articulation surfaces of the first components of the first group each have the same radius.

5. The intervertebral implant according to claim 2 wherein the concave spherical articulation surface of the first components of the first group each have different radii.

6. The intervertebral implant according to claim 1, wherein the shortest distance between the center of rotation and the second surface is no less than 0.5 mm inside of the second component.

7. The intervertebral implant according to claim 1, wherein the distance between the center of rotation and the second surface is no less than 1 mm outside of the second component.

8. The intervertebral implant according to claim 1, wherein the shortest distance between the center of rotation and the second surface is less than six-hundred percent of the overall height of the intervertebral implant.

9. The intervertebral implant according to claim 1, wherein the first and second components each have a mutually facing intermediate surface and wherein these intermediate surfaces are tiltable relative to each other within a range of zero degrees to twelve degrees.

10. A kit for creating a modular intervertebral implant for insertion between two adjacent vertebral bodies comprising:

a first group of first components with unequal heights wherein each first component has a first height $H_1$ and comprises a first surface configured to contact at least a portion of an end plate of the first adjacent vertebral body; and a concave spherical articulation surface with a radius R; and a second group of second components with unequal heights wherein each second component has a second height $H_2$ and comprises a second surface configured to contact at least a portion of an end plate of the second adjacent vertebral body, and a convex spherical articulation surface with substantially the same radius R as the concave spherical articulation surface; wherein:

each first component and second component are connectable in a ball-joint like manner to form an intervertebral implant, and wherein a selected first component and selected second component form a center of rotation RZ for said intervertebral implant which center of rotation RZ differs based on the first component and second component selected; and wherein the center of rotation RZ has a shortest distance A to the second surface that is equal to the absolute difference between the height $H_2$ of the second component and the radius R of the second component selected; and wherein a maximum overall H of the intervertebral implant is less than $H_1+H_2$.

11. The kit according to claim 10, wherein the sum ($H_1+H_2$) of the first height and the second height is constant for predetermined combinations of a first component with a second component.

12. The kit according to claim 10, wherein all of the components of the first and second groups have the same radius.

13. The kit of claim 10, wherein the concave spherical articulation surfaces of each of the first components of the first group each have the same radius.

14. The kit of claim 10 wherein the concave spherical articulation surface of the first components of the first group each have different radii.

15. The kit of claim 10, wherein the first and second components each have a mutually facing intermediate surface and wherein these intermediate surfaces are tiltable relative to each other within a range of zero degrees to twelve degrees.

* * * * *